US005455278A

United States Patent [19]
Parreiras et al.

[11] Patent Number: 5,455,278
[45] Date of Patent: Oct. 3, 1995

[54] METHOD OF INHIBITING PATHOGENS AND FOOD SPOILAGE BACTERIA

[75] Inventors: June F. M. Parreiras, Vicosa, Brazil; Eric A. Johnson, Madison, Wis.

[73] Assignee: Wisconsin Alumni Research Foundation, Madison, Wis.

[21] Appl. No.: 308,779

[22] Filed: Sep. 19, 1994

[51] Int. Cl.⁶ .............................. A01N 31/14; A23L 3/34
[52] U.S. Cl. ........................................... 514/723; 426/532
[58] Field of Search ............................ 514/723; 426/532

[56] References Cited

U.S. PATENT DOCUMENTS

| | | | |
|---|---|---|---|
| 5,019,411 | 5/1991 | Johnson et al. | 426/52 |
| 5,186,962 | 2/1983 | Hutkins et al. | 426/61 |

OTHER PUBLICATIONS

Kern, J. et al. J. Nat. Prod. (1982), 45(6) 774–6.
Chem Abst. 99: 218453 1983
Chem Abst. 100: 179998 1983.
Chem Abst. 105: 178278 1986.
Chem Abst. 120: 161851 1994.
Chem Abst. 120: 50203 1993.
Chem Abst. 119: 133474 1993.
Crosby, D. G., et al, "The Structure of Carotatoxin, A Natural Toxicant From Carrot" Tetrahedron, (1967), vol. 23 pp. 465–472.
Garrod, B., et al, "Studies On The Mechanism Of Action Of The Antifungal Compound Falcarindiol" New Phytol. (1979) 83, pp. 463–471.
Garrod, et al, "Effect of Falcaridinol on Hyphal Growth of Mycocentrospora Acerina" Trans. Br. Mycol. Soc. (1982) 78 (3) pp. 533–536.
Garrod, et al, "Probable Role of Oil Ducts in Carrot Root Tissue" Trans. Br. Mycol. Soc. (1980) 75 (1) pp. 166–169.
Mercier, et al., "Polyacetylene content and UV–Induced 6–Methoxymellein Accumulation in Carrot Cultivars" J. Sci Food Agric (1993), 63, pp. 313–317.
Harding, V. K., et al., "The Accumulation of Inhibitory Compounds In The Induced Resistance Response of Carrot Root Slices to Botrytis Cinerea" Physiological Plant Pathology (1981), 18, pp. 7–15.
Davis, et al., "Antifungal Activity in Carrot Roots in Relation to Storage Infection by Mycocent Rospora Acarina (Hartig) Deighton" New Phytol. (1981) 88 pp. 109–119.

*Primary Examiner*—Paul J. Killos
*Attorney, Agent, or Firm*—Quarles & Brady

[57] ABSTRACT

A method of inhibiting gram-positive bacteria in a medium, such as food, comprises adding to the medium an effective amount of an inhibitor from carrots or a derivative thereof. Compositions and products containing such an inhibitor are also disclosed.

10 Claims, No Drawings

METHOD OF INHIBITING PATHOGENS AND FOOD SPOILAGE BACTERIA

FIELD OF THE INVENTION

This invention relates to a method of inhibiting microbial pathogens and food spoilage microorganisms. More particularly, it relates to a method of inhibiting Listeria and other gram-positive foodborne pathogens and spoilage organisms with an inhibitor from carrots and to food products and pharmaceutical compositions containing the inhibitor.

BACKGROUND OF THE INVENTION

The presence of bacterial pathogens in foods is a major concern to the food processing industry, government regulatory agencies and consumers. Foodborne pathogens are known to have been responsible for food poisoning outbreaks, some of which have resulted in serious illness and death. In addition, the presence of pathogens and spoilage organisms in foods has led to numerous product recalls, product losses, and considerable negative publicity for the food industry.

For example, it has been shown that *Listeria monocytogenes*, a potent pathogen, occurs commonly in dairy foods, seafoods, poultry, and meats, including cured and fermented meats. Furthermore, it has been proved that *Listeria monocytogenes* can contaminate industrially processed foods, along the packaging line as in the case of ice creams, vegetables in bags and salted meats. Post-processing contamination is a major route of contamination of foods.

There is an obvious need for an effective method of inhibiting pathogens, especially Listeria and other gram-positive organisms, in food, as well as, a need for food products that are resistant to infection by such pathogens. It would be especially advantageous if the pathogens could be controlled using an inhibitor from a natural source.

BRIEF SUMMARY OF THE INVENTION

It is an object of the present invention to disclose a method of inhibiting food pathogens and spoilage organisms with an inhibitor from a natural source.

It also is an object to disclose foods containing an effective amount of a food pathogen and spoilage organism inhibitor from a natural source.

It is a further object to disclose novel pharmaceutical compositions containing a food pathogen and spoilage organism inhibitor from a natural source.

We have discovered that falcarindiol, a naturally occurring compound found in carrots, is a potent food pathogen and food spoilage organism inhibitor, especially effective against the gram-positive organisms *Listeria*, *Clostridium botulinum* and *Staphylococcus aureus*. In addition to falcarindiol, which is a natural polyacetylene, its homologs and derivatives which may be represented by the following formula are useful as inhibitors for food pathogens:

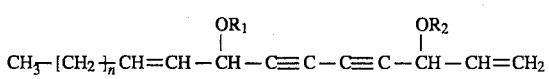

in which $R_1$ and $R_2$ are the same or different and selected from hydrogen and an alkyl of 1 to 6 carbon atoms, such as methyl, ethyl, n-butyl, or hexyl, and n is 4 to 8. When $R_1$ and $R_2$ are hydrogen and n is 6 the compound is falcarindiol.

The novel method of the present invention for inhibiting a food pathogen or spoilage organism, such as Listeria, in a medium, such as food or food packaging, basically comprises introducing into the medium a safe amount of an inhibitor of Formula I which is effective to inhibit the Listeria or other food pathogens or spoilage organisms that may contact or be present in or may later enter the medium.

The novel food products of the present invention are those which contain added amounts of an inhibitor of Formula I which are safe and effective to inhibit the growth of food pathogens or spoilage organisms.

The novel pharmaceutical compositions are those which, in addition to conventional diluents, contain an effective amount of an inhibitor of Formula I.

The preferred inhibitor for use in the method, the food products and the pharmaceutical compositions is falcarindiol which surprisingly inhibits Listeria in concentrations of as low as 1 ppm to 3 ppm. Normally, the falcarindiol will be used or present in amounts ranging from about 0.5 ppm to 50 ppm.

Some of the advantages of using falcarindiol as the inhibitor are that it is a natural food component, it is effective at pH (acidity) values above 5, it is active under aerobic conditions and it can be inactivated by heating. In addition, it is readily soluble in ethyl acetate which can be used as a flavoring agent in food and pharmaceuticals and it is soluble in other solvents, especially those with higher dielectric constants (6.0 to 9). Therefore, it can be easily formulated into novel pharmaceutical and veterinary compositions for use in animals, including humans.

It will be apparent to those skilled in the art that the above described and additional objects and advantages may be obtained by the practice of the present invention.

DESCRIPTION OF THE PREFERRED EMBODIMENTS

The preferred method of the present invention comprises incorporating a safe and effective amount of falcarindiol into a medium, such as food, to inhibit gram-positive bacterial growth.

"Safe and effective amount" as used herein means an amount of the compound which is enough to provide the desired inhibition, but not so high as to cause undesirable other properties, such as an unacceptable taste. The safe and effective amount will vary with the particular inhibitor chosen, and the taste or flavoring of the particular medium, such as food, to which the inhibitor is to be added.

Other inhibitors and agents, which do not interfere with the desired inhibition of the pathogens also can optionally be added in the method of this invention.

The falcarindiol preferred for use in the present invention is extracted from a natural source, carrots, and it may be used as a pure compound or as a carrot extract. In addition, synthetic falcarindiol can be used.

Falcarindiol is found to be present in many varieties of carrots, albeit in different concentrations. The compound is found in higher amounts in yellow carrots and in small carrots. Also, extracts from skin sections of the carrots contain more falcarindiol and are thus more inhibitory than extracts from the interior sections of the carrot root. Similarly, extracts from the crown and tip sections of carrots contain more falcarindiol and are more active than extracts from the middle section.

The exact mechanism by which falcarindiol inhibits pathogens is not known. However, transmission electron microscopy images of *Listeria monocytogenes* cells treated with falcarindiol showed that the compound affected the cell envelope, causing leakage of intracellular materials. In addition, patch clamp technique studies on giant spheroplasts of *E. coli* treated with falcarindiol showed that mechanosensitive channels were activated by this compound.

The practice of the present invention is further illustrated by the description and examples which follows:

MATERIALS AND METHODS

Carrots

Whole carrot roots, *Daucus carota* L., "Imperator" type were purchased from a local supermarket.

Solvents

Hexane, petroleum ether, ethyl acetate and methylene chloride were used for extraction.

Bacteria, growth media and enumeration

Stock cultures of *L. monocytogenes* Scott A were maintained on Brain Heart Infusion (BHI) agar (Difco Laboratories, Detroit, Mich.) and stored at 4° C. Inocula were developed by suspension of a loopful of cells in 10 ml BHI broth (Difco Laboratories, Detroit, Mich.) in tubes (1.0×12.5 cm). The tube was incubated at 20° C. until the culture reached an $A_{600nm}$ of ~1.0. The turbidity at 600nm was monitored using a Spectronic 20D instrument (Milton Roy Co., Rochester, N.Y.). The initial inoculum of *L. monocytogenes* Scott A was $10^7$ colony forming units (CFU)/ml. Tubes were incubated at 20° C. *L. monocytogenes* was enumerated by plating dilutions on BHI agar which were incubated at 30° C. for 48 hours.

EXAMPLE 1

Preparation of Carrot Extracts

Carrots roots were sliced into disks (4 mm thick) using a food processor, covered with an organic solvent selected from hexane, petroleum ether, ethyl acetate and methylene chloride (1 part carrot to 2 parts solvent) and allowed to stand at 4° C. in the dark. After 36 to 48 hours, the suspension was transferred to a separatory funnel. The phases were separated after gentle shaking, and the organic phase solvent was dried over anhydrous $Na_2SO_4$. The extract was filtered using a Whatman #40 paper disc and the volume of the filtrate reduced under vacuum in a rotatory evaporator at temperatures below 30° C. The concentrated solution was reextracted with ethanol which was then evaporated to dryness under $N_2$ at temperatures below 30° C. The dried material was redissolved in absolute ethanol and centrifuged to remove any precipitated material. All procedures were conducted in subdued light.

EXAMPLE 2

Inhibition of *L. monocytogenes* with Carrot Extracts

Ethanolic solutions from the extractions of Example 1 were added to tubes containing $10^7$ CFU/ml in BHI, to give an extract having a final concentration of ethanol of 1% in every experiment. This concentration of ethanol alone did not have significant inhibitory activity against *L. monocytogenes* in BHI. The solvents extracted the inhibitory compound to different degrees. After extraction, the carrot tissue and extracts showed colors varying from light yellow to orange. The ability of each solvent extract in inhibiting *L. monocytogenes* growth was evaluated. The ethyl acetate and methylene chloride extracts gave stronger inhibition than hexane and petroleum ether.

The extracts acted very rapidly on *L. monocytogenes*: immediately after addition of the extract a 2 log inactivation was observed. A 4 log inactivation was found with the ethyl acetate and methylene chloride extracts as compared to the controls. Within an hour, the entire population of $10^7$ *L. monocytogenes* was inactivated.

EXAMPLE 3

Isolation of Falcarindiol

Thin-layer chromatography (TLC) systems were used in order to purify the antilisterial compound(s). Ethyl acetate was used as the extraction solvent. After extraction, filtration and evaporation, the extract was dissolved in ethyl acetate instead of ethanol. The ethyl acetate extract was evaporated under nitrogen, yielding an oily residue that was applied to TLC precoated silica gel plates (Kieselgel 60, F-254 Merck). The plates were initially developed in solvent system (A) consisting of hexane-acetone (2.5:1.0, v/v). Bands were visualized by illumination with visible and UV (254 and 366 nm) light.

Bands were scraped off from the TLC plates and eluted with absolute ethanol. The eluates were transferred to tubes and centrifuged to remove the silica, and the ethanol in the supernatant was evaporated from samples using a gentle stream of $N_2$. The compounds eluted from the bands were tested for their antilisterial activity.

The second step of purification involved application of the partially purified compound to TLC plates and separation with a solvent system (B) consisting of acetone:hexane:chloroform (1:4:6, v/v).

Once the $R_f$ of the antilisterial compound was known, the procedure for purification was slightly modified as follows: after TLC using solvent system A, a region corresponding to $R_f=0.31–0.57$ was scraped off, eluted with ethanol and reapplied in TLC plates for a second run using the same solvent system A. The antilisterial compound appeared as a wide band with the $R_f$ limits being 0.43–0.49. It was visible as a brown band and was easily identified by inspection under UV light. At $UV_{366nm}$, but not in visible light, a bright yellow band appeared immediately above it. In addition, it was located above a thin brown band that was observed under both $UV_{366nm}$ and visible light. The antilisterial band was scraped off, eluted with ethanol and centrifuged. The supernatant solution was evaporated under $N_2$, applied to a TLC plate and developed using solvent system B. Elution of the antilisterial band and development on a fresh TLC plate in the same solvent system B were carried out to check if only a single compound was present and to ensure purity before spectral measurements and identification procedures.

Visible and UV Spectroscopy

Visible and UV absorbance measurements were made on a Cary 3 spectrophotometer with a temperature controller. The absorbance spectrum was representative of polyacetylenes showing absorption peaks at 214, 231, 244, 258, 268 and 294 nm.

Gas-Chromatography-Mass Spectrometry

The purified compound was submitted for gas chromatography coupled to mass spectroscopy at the State Laboratory of Hygiene at the University of Wisconsin-Madison. A Finnigan 4500 GC/MS, equipped with a DB-5 column of 30 m length, 0.32 mm inner diameter and 1 µm film thickness (J&W Scientific) was operated in the electron ionization mode with an electron energy of 70 eV, electron multiplier (EM) voltage of 940 V, emission current of 0.32 ma, and an ion source temperature of 150° C. All data were acquired and stored using a NOVA/4X computer (Data General) and analyzed using the most current version of the Finnigan 4500 software. Helium was used at a head pressure of 10 lbs. The initial temperature of 50° C. was held for 1 minute, and then ramped to 270° C. at 20° C./min. The mass range from 34–450 atomic units mass (amu) was scanned every second. A total of 1716 scans (1716 seconds) were made. The compound was determined to have a molecular weight of 260.

Chemical Ionization

The purified compound was submitted for chemical ionization at the State Laboratory of Hygiene at the University of Wisconsin-Madison. A Finnigan 4500 GC/MS, equipped with a DB-5 column of 15 m length, 0.25 mm inner diameter and 1 μm film thickness (J&W Scientific) was operated in the chemical ionization mode with an electron energy of 100 eV, electron multiplier (EM) voltage of 1.55 kV, emission current of 0.1 ma and an ion source temperature of 100° C. All data were acquired, stored and analyzed as described above. The GC carrier gas was helium at a head pressure of 10 lbs and the CI gas was methane. The initial temperature was 50° C., which was held for 1 minute, and then ramped to 270° C. at 20° C./min. The mass range from 100–450 atomic units mass (amu) was scanned every second The amu was confirmed to be 261.

NMR Spectroscopy

The purified compound was dried to completion, resuspended in deuterated chloroform ($CDCl_3$) and submitted for $^1H$ NMR and $13_{c\ NMR}$ analysis at the NMR Facility at the University of Wisconsin-Madison (NMRFAM). One-dimensional spectra were obtained at 500MHz for $^1H$ NMR and 125.7 MHz for $^{13}C$ NMR at a temperature of 300° K. Assignment of the peaks demonstrated that the structure was in accordance with falcarindiol.

Gas Liquid Chromatography (GLC)

Since pure standards of falcarindiol were not available, a final experiment to confirm the identity was conducted. Gas liquid chromatography was set up using identical conditions as those previously reported for the isolation and identification of falcarindiol. Methyl-palmitate was employed as an internal standard. Values found for the relative retention index were within 5% of the published data. The ethanolic extract was analyzed using GLC with a glass column (10.36 ft by 1/16 in.) packed with 3% OV-17 (Supelco Inc.) on 100–120 mesh Chromosorb W-HP and a Varian model 1700 gas chromatograph equipped with a flame ionization detector (temperature, 250° C.; hydrogen, 20 ml/min; air, 300 ml/min). Helium was used as the carrier gas (15 ml/min). The column oven temperature was programmed from 80° C. to 250° C. at 4° C./min with a 5-min final hold. Methyl palmitate was used as the internal standard. The compound eluted at the same retention time as described in earlier chemical studies.

Comparison of UV, mass and NMR spectra and relative retention index obtained from gas chromatography with data previously reported for pure standards of polyacetylenes from carrots, thus the identity of the antilisterial substance as falcarindiol was confirmed.

EXAMPLE 4

Inhibitory Effect of Falcarindiol from Carrots On Different Food-borne Pathogens Bacterial cells were prepared for inocula as described previously. Purified falcarindiol from carrots dissolved in absolute ethanol was added at various concentrations (0.5%, 1% or 2%) to the tubes. One hundred microliters of a culture with $A_{600nm}$~1.0 was added to the tubes. For *C. botulinum* experiments, anaerobic procedures were employed for the preparation of the medium, addition of the carrot compound and inoculation of the bacterium. For the other bacteria, aerobic conditions were used. Tubes were incubated at 20° C. and cell growth monitored by following the optical density at 600nm.

The ability of the falcarindiol in inhibiting certain food-borne pathogens including *Salmonella typhimurium, Escherichia coli, Clostridium botulinum* and *Staphylococcus aureus* was evaluated. Two concentrations levels of the antilisterial compound were tested for each microorganism. Experiments with *C. botulinum* were conducted under anaerobic conditions. The isolated falcarindiol from carrots inhibited *C. botulinum* and *S. aureus* but was inactive against *E. coli* and *S. typhimurium*. These results suggest that the falcarindiol was innocuous to these gram-negative bacteria. Although both *S. aureus* and *C. botulinum* were inhibited, the experiments with *C. botulinum* are not readily comparable to those with *S. aureus* because they were conducted under anaerobic conditions and the effect of the antimicrobial compound is decreased under these conditions. However, even then, the inhibitory effect of the compound was clear. The data from a screening of the effectiveness of falcarindiol against different bacterial strains suggests a MIC (minimum inhibitory concentration) of about 1 to about 5 ppm.

EXAMPLE 5

Effect of Oxygen on the Inhibitory Activity of Falcarindiol

Oxygen has been demonstrated to be an important factor in the physiology of food-borne pathogens. This molecule is not only involved in the survival of food-borne pathogens but can also be transformed to toxic metabolites. To evaluate the influence of oxygen on inhibition by falcarindiol in the carrot extract, L. monocytogenes was grown at pH 7.5 and 20° C. in the presence of the compound under anaerobic and aerobic conditions. Inhibition was much greater under aerobic conditions and L. monocytogenes was completely inactivated. Under anaerobic conditions, a lag phase of 15 hours was observed, after which the cells grew at a similar rate as the control. It should be noted that the aerobic control grew at rate faster than the anaerobic control, thus making the difference in the activity of falcarindiol even more pronounced.

Representative of food products (media) which can be protected by the method of the present invention are the following:

A. Animal derived foods
   meats
   fish
   eggs
   milk
   cheese processed foods
B. Vegetable derived foods
   vegetables
   fruits
   juices The falcarindiol and other inhibitors of Formula 1 also can be employed in amounts ranging from 0.5 ppm to 300 ppm in combination with acceptable diluents or pharmaceutical and veterinary compositions such as tablets, capsules, tonics, toothpastes, mouthwashes, lotions, creams, ointments and gels. Such compositions can be used to treat a wide variety of conditions caused by gram-positive bacteria.

The falcarindiol, in addition to being a natural food component and very active as an inhibitor of the gram-positive food pathogens is very safe. The $LD_{50}$ for falcarindiol in mice is about 100mg/kg of body weight. Its human toxicity can be expected to be low since certain individuals eat several pounds of carrots daily.

It will be readily apparent to those skilled in the art that a number of modifications and changes can be made without departing from the spirit and scope of the invention. Therefore, it is intended that the invention be limited only by the claims.

We claim:

1. A method of inhibiting gram-positive bacteria in a medium which comprises adding to the medium an inhibitor having the following formula:

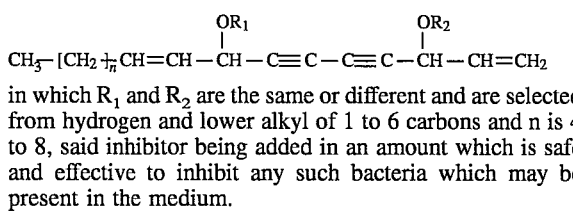

in which $R_1$ and $R_2$ are the same or different and are selected from hydrogen and lower alkyl of 1 to 6 carbons and n is 4 to 8, said inhibitor being added in an amount which is safe and effective to inhibit any such bacteria which may be present in the medium.

2. A method of claim 1 in which the medium is a food of animal origin.

3. A method of claim 1 in which the medium is a food of vegetable origin.

4. A method of claim 1 in which the medium is processed food.

5. A method of claim 1 in which the medium is a meat.

6. A method of claim 1 in which the inhibitor is falcarindiol.

7. A food product containing an amount effective to inhibit gram-positive bacteria of an inhibitor of the following formula:

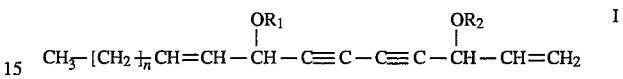

in which $R_1$ and $R_2$ are the same or different and are selected from hydrogen and lower alkyl of 1 to 6 carbons and n is 4 to 8.

8. A pharmaceutical composition for inhibiting gram-positive bacteria infections in an animal, said composition comprising a pharmaceutical diluent and a safe amount of an inhibitor of the formula:

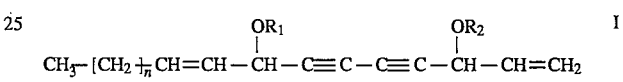

in which $R_1$ and $R_2$ are the same or different and are selected from hydrogen and lower alkyl of 1 to 6 carbons and n is 4 to 8, said amount being effective to inhibit gram-positive bacteria.

9. A composition of claim 8 which is a preparation for topical use.

10. A composition of claim 8 in which the inhibitor is falcarindiol.

* * * * *